United States Patent [19]

Hasegawa et al.

[11] Patent Number: 4,977,275
[45] Date of Patent: Dec. 11, 1990

[54] PYRROLE DERIVATIVES

[75] Inventors: Hiroshi Hasegawa, Narita; Kinichi Mogi, Abiko; Noriaki Shioiri, Narita; Susumu Sato, Shisui; Tatsuhiko Katori, Tone, all of Japan

[73] Assignee: SS Pharmaceutical Co., Ltd., Tokyo, Japan

[21] Appl. No.: 333,239

[22] Filed: Apr. 5, 1989

[30] Foreign Application Priority Data

Apr. 5, 1988 [JP] Japan ................... 63-84328

[51] Int. Cl.$^5$ .................................. C07D 207/30
[52] U.S. Cl. .................................. 548/539; 546/281; 548/517; 548/527
[58] Field of Search ......................... 548/539

[56] References Cited

U.S. PATENT DOCUMENTS 4,000,160 12/1976 Bailey ..................... 548/539

FOREIGN PATENT DOCUMENTS 0159763 10/1982 Japan ..................... 548/539
0038361 2/1985 Japan ..................... 548/539

OTHER PUBLICATIONS

Ezaki, et al., C.A. 100:64648h (1984).
Durham, et al., C.A. 78:4053c (1973).

Primary Examiner—Joseph Paul Brust
Attorney, Agent, or Firm—Oblon, Spivak, McClelland, Maier & Neustadt

[57] ABSTRACT

A pyrrole derivative having excellent anti-microbial activities is disclosed. This compound is represented by the following formula (I):

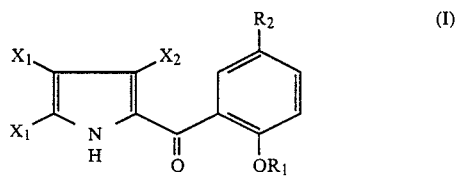

wherein $X_1$ and $X_2$ are the same or different and mean individually a halogen atom, $R_1$ denotes an alkyl, cycloalkyl, haloalkyl, alkenyl, substituted or unsubstituted phenyl, substituted or unsubstituted aralkyl group or a group —$COR_3$ in which $R_3$ is an alkyl group having at least five carbon atoms or a cycloalkyl, haloalkyl, alkenyl, substituted or unsubstituted phenyl, substituted or unsubstituted aralkyl, or heterocyclic group, and $R_2$ stands for a hydrogen or halogen atom or an alkyl group, with a proviso that $R_1$ is other than a hydrogen atom or methyl group when $X_1$, $X_2$ and $R_2$ are each a bromine atom.

1 Claim, No Drawings

PYRROLE DERIVATIVES

BACKGROUND OF THE INVENTION

1. Field of the Invention

This invention relates to novel pyrrole derivatives, and more specifically to pyrrole derivatives which have excellent antimicrobial activities against bacteria, Trichophyton, pathogenic fungi for plants, etc. and are usable as pharmaceutical products, agricultural chemicals, antiseptics and the like.

2. Description of the Related Art

Pyrrolomycins have heretofore been known as pyrrole derivatives having antimicrobial activities against bacteria, Trichophyton, and pathogenic fungi for plants (Japanese Patent Application Laid-Open No. 126863/1983). Their effects are however still not fully satisfactory, resulting in a desire for the development of a compound having even better effects.

SUMMARY OF THE INVENTION

The present inventors have synthesized a variety of pyrrole derivatives and have investigated their antibacterial effects. As a result, it has been found that the pyrrole derivatives represented by the below-described formula (I) have excellent antimicrobial activities against bacteria, Trichophyton, pathogenic fungi for plants, etc., leading to completion of this invention.

This invention therefore provides a pyrrole derivative represented by the following formula (I):

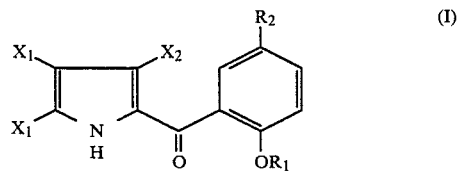

wherein $X_1$ and $X_2$ are the same or different and mean individually a halogen atom, $R_1$ denotes an alkyl, cycloalkyl, haloalkyl, alkenyl, substituted or unsubstituted phenyl, substituted or unsubstituted aralkyl group or a group —$COR_3$ in which $R_3$ is an alkyl group having at least five carbon atoms or a cycloalkyl, haloalkyl, alkenyl, substituted or unsubstituted phenyl, substituted or unsubstituted aralkyl, or heterocyclic group, and $R_2$ stands for a hydrogen or halogen atom or an alkyl group, with a proviso that $R_1$ is other than a hydrogen atom or methyl group when $X_1$, $X_2$ and $R_2$ are each a bromine atom.

The compounds (I) of this invention obtained as described above exhibit excellent antimicrobial activity against bacteria, Candida, Trichophyton and pathogenic fungi for plants, and are hence useful as pharmaceutical products, agricultural chemicals and antiseptics.

DETAILED DESCRIPTION OF THE INVENTION

The compound (I) of this invention can be prepared, for example, by any one of the following processes:

Process 1

A compound (Ia) is prepared by iodinating a pyrrole derivative (III) in accordance with the following formula:

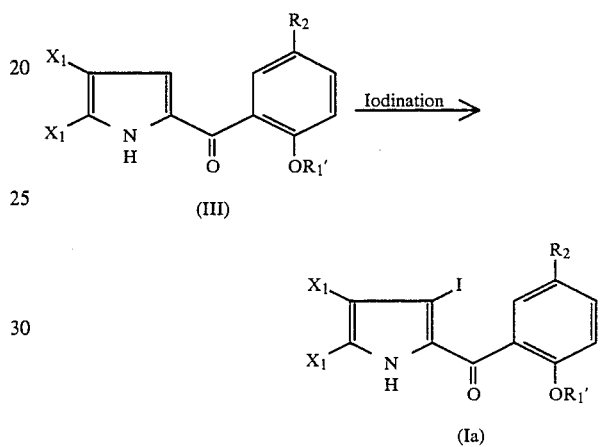

wherein $X_1$ and $R_2$ have the same meanings as defined above, and $R'_1$ denotes an alkyl, cycloalkyl, haloalkyl, alkenyl, substituted or unsubstituted phenyl or substituted or unsubstituted aralkyl group.

The above reaction can be conducted easily by reacting iodine with the pyrrole derivative (III) in the presence of sodium iodide or potassium iodide in a mixed solvent such as dioxane-water.

Examples of the combination of the starting compound (III) in this process and the compound (Ia) obtained by this process are given in Table 1.

TABLE 1

| Starting compound (III) | Invention compound (Ia) |
| --- | --- |
| 2-(2-Methoxybenzoyl)-4,5-dichloropyrrole | 2-(2-Methoxybenzoyl)-3-iodo-4,5-dichloropyrrole |
| 2-(2-n-Butoxybenzoyl)-4,5-dichloropyrrole | 2-(2-n-Butoxybenzoyl)-3-iodo-4,5-dichloropyrrole |
| 2-(2-Octyloxybenzoyl)-4,5-dichloropyrrole | 2-(2-Octyloxybenzoyl)-3-iodo-4,5-dichloropyrrole |
| 2-(2-Cyclopentyloxybenzoyl)-4,5-dichloropyrrole | 2-(2-Cyclopentyloxybenzoyl)-3-iodo-4,5-dichloropyrrole |
| 2-(2-Phenoxybenzoyl)-4,5-dichloropyrrole | 2-(2-Phenoxybenzoyl)-3-iodo-4,5-dichloropyrrole |
| 2-(2-Phenoxy-5-methylbenzoyl)-4,5-dichloropyrrole | 2-(2-Phenoxy-5-methylbenzoyl)-3-iodo-4,5-dichloropyrrole |
| 2-[2-(4-Methylphenoxy)benzoyl]-4,5-dichloropyrrole | 2-[2-(4-Methylphenoxy)benzoyl]-3-iodo-4,5-dichloropyrrole |
| 2-[2-(2-Chloroethoxy)benzoyl]-4,5-dichloropyrrole | 2-[2-(2-Chloroethoxy)benzoyl]-3-iodo-4,5-dichloropyrrole |
| 2-(2-Allyloxybenzoyl)-4,5-dichloropyrrole | 2-(2-Allyloxybenzoyl)-3-iodo-4,5-dichloropyrrole |
| 2-[2-(1-Propenyloxy)benzoyl]-4,5-dichloropyrrole | 2-[2-(1-Propenyloxy)benzoyl]-3-iodo-4,5-dichloropyrrole |
| 2-(2-Methoxy-5-fluorobenzoyl)-4,5-dichloropyrrole | 2-(2-Methoxy-5-fluorobenzoyl)-3-iodo-4,5-dichloropyrrole |
| 2-(2-Benzyloxybenzoyl)-4,5-dichloropyrrole | 2-(2-Benzyloxybenzoyl)-3-iodo-4,5-dichloropyrrole |
| 2-[2-(4-Methoxybenzyloxy)benzoyl]-4,5-dichloropyrrole | 2-[2-(4-Methoxybenzyloxy)benzoyl]-3-iodo-4,5-dichloropyrrole |

Process 2

A compound (Ib) is prepared by halogenating a pyrrole derivative (II') or (III') in accordance with the following scheme:

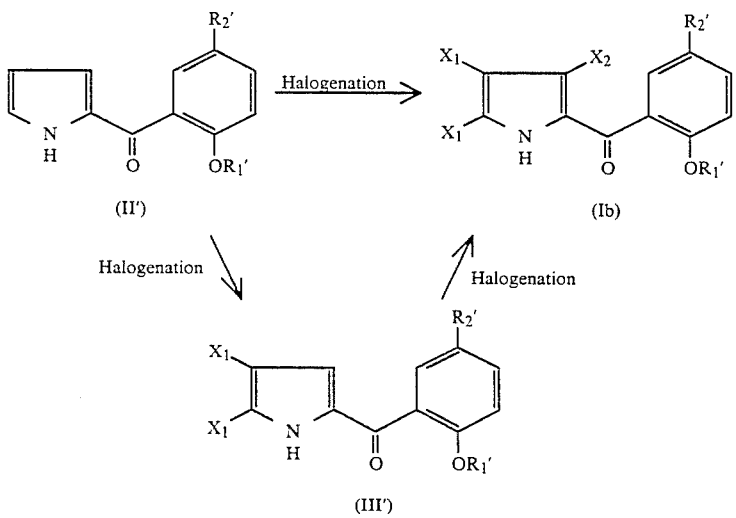

wherein $X_1$ and $X_2$ have the same meanings as defined above, $R'_2$ denotes a halogen atom, and $R'_1$ stands for an alkyl, cycloalkyl or haloalkyl group.

According to this reaction, a halogenating agent is caused to act on the pyrrole derivative (II') in an inert solvent to obtain the compound (Ib) directly, or to conduct partial halogenation to obtain the pyrrole derivative (III'), followed by reaction with a different halogenating agent to obtain the compound (Ib).

As the halogenating agents, t-butylhypochlorite, bromine, chlorine or the like may be used.

Examples of the combination of the starting compound (II') in this process and the compound (Ib) obtained by this process are given in Table 2.

-continued

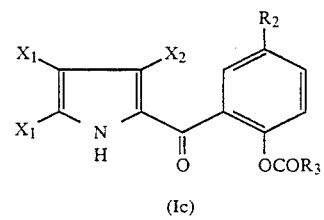

wherein $X_1$, $X_2$, $R_2$ and $R_3$ have the same meanings as defined above.

This reaction is conducted by reacting a conventional

TABLE 2

| Starting compound (II') | Invention compound (Ib) |
| --- | --- |
| 2-(2-Ethoxy-5-bromobenzoyl)pyrrole | 2-(2-Ethoxy-5-bromobenzoyl)-3,4,5-tribromopyrrole |
| 2-(2-Ethoxy-5-fluorobenzoyl)pyrrole | 2-(2-Ethoxy-5-fluorobenzoyl)-3,4,5-tribromopyrrole |
| 2-(2-Cyclopentyloxy-5-bromobenzoyl)pyrrole | 2-(2-Cyclopentyloxy-5-bromobenzoyl)-3,4,5-tribromopyrrole |
| 2-(2-Propoxy-5-chlorobenzoyl)pyrrole | 2-(2-Propoxy-5-chlorobenzoyl)-3,4,5-trichloropyrrole |
| 2-(2-Butoxy-5-fluorobenzoyl)pyrrole | 2-(2-Butoxy-5-fluorobenzoyl)-3-bromo-4,5-dichloropyrrole |
| 2-(2-Butoxy-5-bromobenzoyl)pyrrole | 2-(2-butoxy-5-bromobenzoyl)-3-bromo-4,5-dichloropyrrole |
| 2-(2-Cyclohexyloxy-5-bromobenzoyl)pyrrole | 2-(2-Cyclohexyloxy-5-bromobenzoyl)-3-bromo-4,5-dichloropyrrole |
| 2-(2-Cyclohexyloxy-5-chlorobenzoyl)pyrrole | 2-(2-Cyclohexyloxy-5-chlorobenzoyl)-3-bromo-4,5-dichloropyrrole |
| 2-(2-Hexyloxy-5-fluorobenzoyl)pyrrole | 2-(2-Hexyloxy-5-fluorobenzoyl)-3,4,5-tribromopyrrole |
| 2-(2-Hexyloxy-5-bromobenzoyl)pyrrole | 2-(2-Hexyloxy-5-bromobenzoyl)-3-bromo-4,5-dichloropyrrole |
| 2-(2-Nonyloxy-5-bromobenzoyl)pyrrole | 2-(2-Nonyloxy-5-bromobenzoyl)-3,4,5-tribromopyrrole |
| 2-[2-(2,2,2-trifluoroethoxy)-5-fluorobenzoyl]pyrrole | 2-[2-(2,2,2-trifluoroethoxy)-5-fluorobenzoyl]-3,4,5-tribromopyrrole |
| 2-[2-(3-Chloropropoxy)-5-bromobenzoyl]pyrrole | 2-[2-(3-chloropropoxy)-5-bromobenzoyl]-3-bromo-4,5-dichloropyrrole |

Process 3

A compound (Ic) is prepared by acylating a pyrrole derivative (IV) in accordance with the following formula:

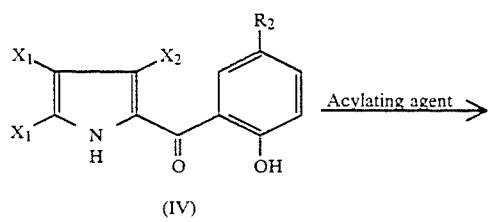

acylating agent, for example, an acid anhydride or acid halide with the compound (IV) in the presence of a base.

Examples of the combination of the starting compound (IV) and acylating agent in this process and the compound (Ic) obtained by this process are given in Table 3.

TABLE 3

| Starting compound (IV) | Acylating agent | Invention compound (Ic) |
| --- | --- | --- |
| 2-(2-Hydroxybenzoyl)-3,4,5-tribromopyrrole | Enanthic anhydride | 2-(2-Heptanoyloxybenzoyl)-3,4,5-tribromopyrrole |
| 2-(2-Hydroxybenzoyl)-3,4,5-tribromopyrrole | Caprylic anhydride | 2-(2-Octanoyloxybenzoyl)-3,4,5-tribromopyrrole |
| 2-(2-Hydroxybenzoyl)-3,4,5-tribromopyrrole | Pelargonic anhydride | 2-(2-Nonanoyloxybenzoyl)-3,4,5-tribromopyrrole |
| 2-(2-Hydroxybenzoyl)-3,4,5-tribromopyrrole | Capric anhydride | 2-(2-Decanoyloxybenzoyl)-3,4,5-tribromopyrrole |
| 2-(2-Hydroxybenzoyl)-3,4,5-tribromopyrrole | Undecanoic acid chloride | 2-(2-Undecanoyloxybenzoyl)-3,4,5-tribromopyrrole |
| 2-(2-Hydroxybenzoyl)-3,4,5-tribromopyrrole | Pentadecanoic acid chloride | 2-(2-Pentadecanoyloxybenzoyl)-3,4,5-tribromopyrrole |
| 2-(2-Hydroxybenzoyl)-3,4,5-tribromopyrrole | Cyclopentanecarboxylic acid chloride | 2-(2-Cyclopentanecarbonyloxybenzoyl)-3,4,5-tribromopyrrole |
| 2-(2-Hydroxybenzoyl)-3,4,5-tribromopyrrole | Cyclohexanecarboxylic acid chloride | 2-(2-Cyclohexanecarbonyloxybenzoyl)-3,4,5-tribromopyrrole |
| 2-(2-Hydroxybenzoyl)-3,4,5-tribromopyrrole | Chloroacetyl chloride | 2-(2-Chloroacetyloxybenzoyl)-3,4,5-tribromopyrrole |
| 2-(2-Hydroxybenzoyl)-3,4,5-tribromopyrrole | 3-Chloropropionic acid chloride | 2-(3-Chloropropionylbenzoyl)-3,4,5-tribromopyrrole |
| 2-(2-Hydroxybenzoyl)-3,4,5-tribromopyrrole | Crotonic anhydride | 2-(2-Crotonoyloxybenzoyl)-3,4,5-tribromopyrrole |
| 2-(2-Hydroxybenzoyl)-3,4,5-tribromopyrrole | Benzoyl chloride | 2-(2-Benzoyloxybenzoyl)-3,4,5-tribromopyrrole |
| 2-(2-Hydroxybenzoyl)-3,4,5-tribromopyrrole | P-Methoxybenzoyl chloride | 2-(2-p-Methoxybenzoylpxybenzoyl)-3,4,5-tribromopyrrole |
| 2-(2-Hydroxybenzoyl)-3,4,5-tribromopyrrole | 3-Phenylpropionyl chloride | 2-[2-(3-Phenylpropionyloxy)benzoyl]-3,4,5-tribromopyrrole |
| 2-(2-Hydroxybenzoyl)-3,4,5-tribromopyrrole | 3-p-Methoxyphenylpropionyl chloride | 2-[2-(3-p-Methoxyphenylpropionyloxy)-3,4,5-tribromopyrrole |
| 2-(2-Hydroxybenzoyl)-3-iodo-4,5-dichloropyrrole | Enanthic anhydride | 2-(2-heptanoyloxybenzoyl)-3-iodo-4,5-dichloropyrrole |
| 2-(2-Hydroxybenzoyl)-3-iodo-4,5-dichloropyrrole | Caprylic anhydride | 2-(2-Octanoyloxybenzoyl)-3-iodo-4,5-dichloropyrrole |
| 2-(2-Hydroxybenzoyl)-3-iodo-4,5-dichloropyrrole | Pelargonic abhydride | 2-(2-Nonanoyloxybenzoyl)-3-iodo-4,5-dichloropyrrole |
| 2-(2-Hydroxybenzoyl)-3-iodo-4,5-dichloropyrrole | Capric anhydride | 2-(2-Decanoyloxybenzoyl)-3-iodo-4,5-dichloropyrrole |
| 2-(2-Hydroxybenzoyl)-3-iodo-4,5-dichloropyrrole | Undecanoic acid chloride | 2-(2-Undecanoyloxybenzoyl)-3-iodo-4,5-dichloropyrrole |
| 2-(2-Hydroxybenzoyl)-3-iodo-4,5-dichloropyrrole | Pentadecanoic acid chloride | 2-(2-Pentadecanoyloxybenzoyl)-3-iodo-4,5-dichloropyrrole |
| 2-(2-Hydroxybenzoyl)-3-iodo-4,5-dichloropyrrole | Cyclopentanecarboxylic acid chloride | 2-(2-Cyclopentanecarbonyloxybenzoyl)-3-iodo-4,5-dichloropyrrole |
| 2-(2-Hydroxybenzoyl)-3-iodo-4,5-dichloropyrrole | Cyclohexanecarboxylic acid chloride | 2-(2-Cyclohexanecarbonyloxybenzoyl)-3-iodo-4,5-dichloropyrrole |
| 2-(2-Hydroxybenzoyl)-3-iodo-4,5-dichloropyrrole | Chloroacetyl chloride | 2-(2-Chloroacetylaxybenzoyl)-3-iodo-4,5-dichloropyrrole |
| 2-(2-Hydroxybenzoyl)-3-iodo-4,5-dichloropyrrole | 3-Chloropropionic acid chloride | 2-[2-(3-Chloropropionyloxy)benzoyl]-3-iodo-4,5-dichloropyrrole |
| 2-(2-Hydroxtbenzoyl)-3-iodo-4,5-dichloropyrrole | Crotonic anhydride | 2-(2-Crotonoyloxybenzoyl)-3-iodo-4,5-dichloropyrrole |
| 2-(2-Hydroxybenzoyl)-3-iodo-4,5-dichloropyrrole | Benzoyl chloride | 2-(2-Benzoyloxybenzoyl)-3-iodo-4,5-dichloropyrrole |
| 2-(2-Hydroxybenzoyl)-3-iodo-4,5-dichloropyrrole | p-Methoxybenzoyl chloride | 2-(2-p-Methoxybenzoyloxybenzoyl)-3-iodo-4,5-dichloropyrrole |
| 2-(2-Hydroxybenzoyl)-3-iodo-4,5-dichloropyrrole | 3-Phenylpropionyl chloride | 2-[2-(3-Phenylpropionyloxy)benzoyl]-3-iodo-4,5-dichloropyrrole |
| 2-(2-Hydroxybenzoyl)-3-iodo-4,5-dichloropyrrole | 3-p-Methoxyphenyl-propionyl chloride | 2-[2-(3-p-Methoxyphenylpropionyloxy)benzoyl]-3-iodo-4,5-dichloropyrrole |
| 2-(2-Hydroxy-5-fluoro-benzoyl)-3,4,5-tribromopyrrole | Enanthic anhydride | 2-(2-Heptanoyloxy-5-fluorobenzoyl)-3,4,5-tribromopyrrole |
| 2-(2-Hydroxy-5-fluoro-benzoyl)-3,4,5-tribromopyrrole | Pelargonic anhydride | 2-(2-Nananoyloxy-5-fluorobenzoyl)-3,4,5-tribromopyrrole |
| 2-(2-Hydroxy-5-fluoro-benzoyl)-3,4,5-tribromopyrrole | Myristic acid chloride | 2-(2-Myristynoyloxy-5-fluorobenzoyl)-3,4,5-tribromopyrrole |
| 2-(2-Hydroxy-5-fluoro-benzoyl)-3,4,5-tribromopyrrole | Cyclopentanecarboxylic acid chloride | 2-(2-Cyclopenanecarbonyloxy-5-fluorobenzoyl)-3,4,5-tribromopyrrole |
| 2-(2-Hydroxy-5-fluoro-benzoyl)-3,4,5-tribromopyrrole | 3-Chloropropionic acid chloride | 2-[2-(3-Chloropropionyloxy)-5-fluorobenzoyl]-3,4,5-tribromopyrrole |
| 2-(2-Hydroxy-5-fluoro-benzoyl)-3,4,5-tribromopyrrole | Crotonic anhydride | 2-(2-Crotonyloxy-5-fluorobenzoyl)-3,4,5-tribromopyrrole |
| 2-(2-Hydroxy-5-fluoro-benzoyl)-3,4,5-tribromopyrrole | Benzoyl chloride | 2-(2-Benzoyloxy-5-fluorobenzoyl)-3,4,5-tribromopyrrole |

TABLE 3-continued

| Starting compound (IV) | Acylating agent | Invention compound (Ic) |
|---|---|---|
| 2-(2-Hydroxy-5-fluorobenzoyl)-3,4,5-tribromopyrrole | p-Toluoyl chloride | 2-(2-p-Toluoyloxy-5-fluorobenzoyl)-3,4,5-tribromopyrrole |
| 2-(2-Hydroxy-5-fluorobenzoyl)-3,4,5-tribromopyrrole | 2-Phenylpropionyl chloride | 2-[2-(3-Phenylpropionyloxy)-5-fluorobenzoyl]-3,4,5-tribromopyrrole |
| 2-(2-Hydroxy-5-methylbenzoyl)-3,4-5-tribromopyrrole | Enanthic anhydride | 2-(2-Heptanoyloxy-5-methylbenzoyl)-3,4,5-tribromopyrrole |
| 2-(2-Hydroxy-5-methylbanzoyl)-3,4-5-tribromopyrrole | Pelargonic anhydride | 2-(2-Nonanoyloxy-5-methylbenzoyl)-3,4,5-tribromopyrrole |
| 2-(2-Hydroxy-5-methylbenzoyl)-3,4-5-tribromopyrrole | Cyclopropanecarboxylic acid chloride | 2-(2-Cyclopropanecarbonyloxy-5-methylbanzoyl)-3,4,5-tribromopyrrole |
| 2-(2-Hydroxy-5-methylbenzoyl)-3,4-5-tribromopyrrole | Crotonic anhydride | 2-(2-Crotonyloxy-5-methylbenzoyl)-3,4,5-tribromopyrrole |
| 2-(2-Hydroxy-5-methylbenzoyl)-3,4-5-tribromopyrrole | Benzoyl chloride | 2-(2-Benzoyloxy-5-methylbenzoyl)-3,4,5-tribromopyrrole |
| 2-(2-Hydroxy-5-methylbenzoyl)-3,4-5-tribromopyrrole | 3-Phenylpropionyl chloride | 2-[2-(3-Phenylpropionyloxy)-5-methylbenzoyl]-3,4,5-tribromopyrrole |
| 2-(2-Hydroxybenzoyl)-3,4,5-tribromopyrrole | 2-Furoyl chloride (Furancarboxylic acid chloride) | 2-[2-(2-furoyloxy)benzoyl]-3,4,5-tribromopyrrole |
| 2-(2-Hydroxybenzoyl)-3-iodo-4,5-dichloropyrrole | 2-Furanoyl chloride (Furancarboxylic acid chloride) | 2-[2-(2-furoyloxy)benzoyl]-3-iodo-4,5-dichloropyrrole |
| 2-(2-Hydroxy-5-fluorobenzoyl)-3,4,5-tribrmompyrrole | 2-Furoyl chloride | 2-[2-(2-furoyloxy)-5-fluorobenzoyl]-3,4,5-tribromopyrrole |
| 2-(2-Hydroxy-5-methylbenzoyl)-3,4,5-tribromopyrrole | 2-Furoyl chloride | 2-[2-(2-furoyloxy)-5-methylbenzoyl]-3,4,5-tribromopyrrole |
| 2-(2-Hydroxybenzoyl)-3,4,5-tribromopyrrole | 2-Thienoyl chloride (Thiophenecarboxylic acid chloride) | 2-[2-(2-Thienoyloxy)benzoyl]-3,4,5-tribromopyrrole |
| 2-(2-Hydroxybenzoyl)-3-iodo-4,5-dichloropyrrole | 2-Thienoyl chloride (Thiophenecarboxylic acid chloride) | 2-[2-(2-Thienoyloxy)benzoyl]-3-iodo-4,5-dichloropyrrole |
| 2-(2-Hydroxy-5-fluorobenzoyl)-3,4,5-tribromopyrrole | 2-Thienoyl chloride (Thiophenecarboxylic acid chloride) | 2-[2-(2-Thienoyloxy)-5-fluorobenzoyl]-3,4,5-tribromopyrrole |
| 2-(2-Hydroxy-5-methylbenzoyl)-3,4,5-tribromopyrrole | 2-Thienoyl chloride )Thiophenecarboxylic acid chloride) | 2-[2-(2-Thienoyloxy)-5-methylbenzoyl]-3,4,5-tribromopyrrole |
| 2-(2-Hydroxybenzoyl)-3,4,5-tribromopyrrole | Nicotinoyl chloride | 2-(2-Nicotinoyloxybenzoyl)-3,4,5-tribromopyrrole |
| 2-(2-Hydroxybenzoyl)-3-iodo-4,5-dichloropyrrole | Nicotinoyl chloride | 2-(2-Nicotinoyloxybenzoyl)-3-iodo-4,5-dichloropyrrole |
| 2-(2-Hydroxy-5-fluorobenzoyl)-3,4,5-tribromopyrrole | Nicotinoyl chloride | 2-(2-Nicotinoyloxy-5-fluorobenzoyl)-3,4,5-tribromopyrrole |
| 2-(2-Hydroxy-5-methylbenzoyl)-3,4,5-tribromopyrrole | Nicotinoyl chloride | 2-(2-Nicotinoyloxy-5-methylbenzoyl)-3,4,5-tribromopyrrole |

Incidentally, each pyrrole derivative (II) as a starting material for Process 2 can be prepared, for example, in accordance with any one of the following reaction formulae: (1) Pyrrole and a benzoic acid halide derivative (V) are reacted in the presence of a Lewis acid (for example, aluminum chloride) in an inert solvent.

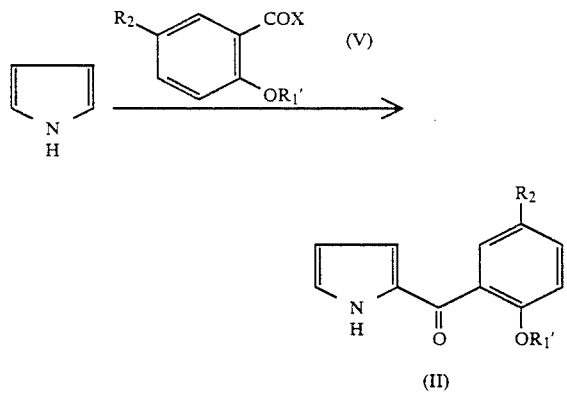

(II)

(2) To a pyrryl magnesium halide (VI) obtained by reacting a Grignard reagent with pyrrole, an alkyl benzoate derivative (VII) is reacted in an inert solvent.

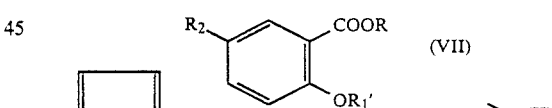

(3) To the compound (VI), a 2-pyridylthiobenzoate derivative (VIII) is reacted in the presence of CuI in an inert solvent.

Further, the pyrrole derivative (III), the starting material for Process 1, can be prepared by halogenating the pyrrole derivative (II).

(II)→(III)

This reaction can be carried out by reacting the pyrrole derivative (II) with a halogenating agent such as sulfuryl chloride in a suitable solvent.

On the other hand, the pyrrole derivative (IV) which is the starting material for Process 3 can be prepared, for example, by subjecting an ester-type derivative (IX) to the Fries rearrangement in accordance with the following formula:

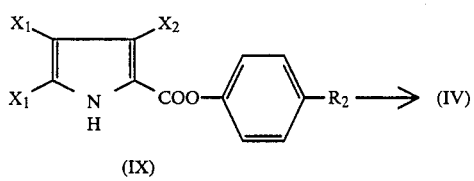

This reaction may be conducted in a manner known per se in the art, for example, at a reaction temperature of 100–200° C. in the presence of a Lewis acid such as aluminum chloride, zinc chloride or tin tetrachloride in an inert solvent, such as carbon disulfide, sulfolane or nitrobenzene.

After the completion of the reaction, the thus-obtained compound (I) of this invention can be purified further by distilling off the solvent and recrystallizing it by a conventional method or if necessary, subjecting it to chromatography or the like.

The compound (I) of this invention can be converted into a pharmaceutically- and/or agriculturally-acceptable inorganic acid salt, organic acid salt or acid addition salt as needed. Examples of the inorganic salt may include the sodium salt, potassium salt, etc.

This invention will hereinafter be described by the following examples.

EXAMPLE 1

Added to 1.08 g of 2-(2-methoxybenzoyl)-4,5-dichloropyrrole were 16 ml of a 1:1 mixture of dioxane and water and 4 ml of a 1 N aqueous solution of sodium hydroxide to dissolve the pyrrole derivative, followed by the addition of 12 ml of an aqueous solution containing 1.2 g of iodine and 1.44 g of sodium iodide. The resultant mixture was stirred at room temperature for 15 hours. Thereafter, 40 ml of a 1 N aqueous solution of sodium thiosulfate was added, followed by stirring for 1 hour. Crystals thus deposited were collected by filtration, washed with water and then dried to obtain 1.24 g of 2-(2-methoxybenzoyl)-3-iodo-4,5-dichloropyrrole (Compound No. 1).

EXAMPLE 2

Dissolved in 5 ml of pyridine was 0.63 g of 2-(2-hydroxybenzoyl)-3,4,5-tribromopyrrole, followed by the addition of 1.5 ml of enanthic anhydride. The resultant mixture was stirred at room temperature for 24 hours. The reaction mixture was poured into 20 ml of ice water, followed by extraction with ether. The extract was washed successively with 1 N hydrochloric acid, a 2% aqueous solution of sodium hydrogen-carbonate, and water. The solution thus washed was dried over anhydrous sodium sulfate and then dried to solid under reduced pressure.

The residue was subjected to chromatography on a silica gel column, and from chloroform eluate fractions, 0.25 g of 2-(2-heptanoyloxybenzoyl)-3,4,5-tribromopyrrole (Compound No. 3) was obtained.

EXAMPLE 3

Compound No. 2 and the compounds numbered 4 ff. shown in Table 4 were obtained in a similar manner as in either one of Examples 1 and 2. Further, physical properties of Compounds 1 and 3 are also shown in the same table.

TABLE 4

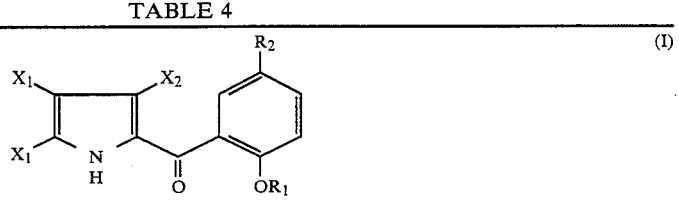

| Compound No. | $X_1$ | $X_2$ | $R_1$ | $R_2$ | Appearance Melting point (°C.) | IR $\nu_{max}^{KBr}$ cm$^{-1}$ | $^1$H-NMR δ ppm (CDCl$_3$) |
|---|---|---|---|---|---|---|---|
| 1 | Cl | I | CH$_3$ | H | Colorless crystals 174–175 | 3230 1620 | 10.20(br,1H), 7.60–6.91(m,4H), 3.78(s,3H). |
| 2 | Br | Br | CH$_3$(CH$_2$)$_5$CO | F | Colorless crystals 68–72 | 3220 1760 1620 | 9.75(br,1H), 7.30–7.08(m,3H), 2.35(t,2H), 1.80–1.05(m,8H), 0.86(t,3H). |
| 3 | Br | Br | CH$_3$(CH$_2$)$_5$CO | H | Colorless crystals 43–47 | 3220 1760 1620 | 9.90(br,1H), 7.65–7.14(m,4H), 2.35(t,2H), 1.82–1.00(m,8H), 0.86(t,3H). |
| 4 | Br | Br | CH$_3$(CH$_2$)$_8$CO | H | Colorless crystals 71–73 | 3220 1760 1620 | 9.60(br,1H), 7.70–7.10(m,4H), 2.38(t,2H), 1.78–1.05(m,14H), 0.86(t,3H). |
| 5 | Br | Br | C$_6$H$_5$CO | H | Colorless crystals 161–163 | 3225 1730 1610 | 9.75(br.1H), 8.08–7.87(m,2H), 7.70–7.20(m,7H). |
| 6 | Cl | I | CH$_3$(CH$_2$)$_5$CO | H | Colorless crystals 70–72 | 3220 1760 1620 | 10.12(br,1H), 7.68–7.16(m,4H), 2.21(t,2H), 1.76–1.08(m,8H), 0.90(t,3H). |
| 7 | Cl | I | CH$_3$(CH$_2$)$_8$CO | H | Colorless crystals 50–58 | 3220 1760 1620 | 10.00(br,1H), 7.68–7.18(m,4H), 2.40(t,2H), 1.76–1.08(m,14H), 0.89(t,3H). |
| 8 | Cl | I | C$_6$H$_5$CO | H | Colorless crystals 145–147 | 3230 1730 1615 | 9.78(br.1H), 7.96(d.d,2H), 7.72–7.16(m,7H). |

TABLE 4-continued

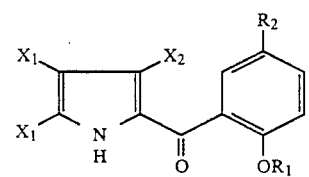
(I)

| Compound No. | In formula (I) | | | | Appearance Melting point (°C.) | IR $\nu_{max}^{KBr}$ cm$^{-1}$ | $^1$H-NMR δ ppm (CDCl$_3$) |
|---|---|---|---|---|---|---|---|
| | $X_1$ | $X_2$ | $R_1$ | $R_2$ | | | |
| 9 | Cl | I | Cl(CH$_2$)$_2$CO | H | Colorless syrup | 3220 1750(neat) 1620 | 10.08(br.1H), 7.67–7.19(m,4H), 3.72(t,2H), 2.88(t,2H). |
| 10 | Br | Br | CH$_3$(CH$_2$)$_8$CO | F | Colorless crystals 89–92 | 3220 1750 1620 | 10.00(br,1H), 7.30–7.00(m,3H), 2.38(t,2H), 1.80–1.05(m,14H), 0.88(t,3H). |
| 11 | Br | Br | C$_6$H$_5$CO | F | Colorless crystals 180–181 | 3250 1730 1615 | 9.67(br.1H), 7.96(m,2H), 7.70–7.10(m,6H). |
| 12 | Br | Br | C$_6$H$_5$CO | CH$_3$ | Colorless crystals 168–169 | 3200 1745 1615 | 9.78(br.1H), 7.96(m,2H), 7.70–7.10(m,6H), 2.41(s,3H). |

TEST

With respect to some representative compounds of this invention, their microbial activities were investigated. The results are summarized in Table 5. Pyrrolomycin F$_1$ disclosed in Japanese Patent Application Laid-Open No. 126863/1983 was used as a comparative compound. In Table 5, the compound numbers indicate the same compounds as designated by their corresponding numbers in the above examples.

TABLE 5

| | Minimum inhibitory concentration (MIC; μg/ml) Test Compound | | | |
|---|---|---|---|---|
| Test microorganism | Compound 2 | Compound 6 | Compound 9 | Pyrrolomycin F$_1$ |
| *Bacillus subtilis* ATCC 6633 | <0.2 | 0.39 | <0.2 | <0.2 |
| *Staphylococcus aureus* FDA 209P | <0.2 | 0.39 | <0.2 | <0.2 |
| *Candida albicans* NHL 4019 | 12.5 | 12.5 | 6.25 | >100 |
| *Candida albicans* Yu-1200 | 12.5 | 12.5 | 6.25 | >100 |
| *Saccharomyces cerevisiae* ATCC 9763 | 12.5 | 12.5 | 12.5 | >100 |
| *Helminthosporium sesamum* IAM 5012 | 6.25 | 6.25 | 6.25 | 6.25 |
| *Piricularia oryzae* IAM 5016 | <0.2 | <0.2 | <0.2 | <0.2 |
| *Debaryomyces kloeckeri* IFO 0015 | 12.5 | 12.5 | 12.5 | >100 |

We claim:

1. A pyrrole derivative represented by the following formula (I):

$$\text{(I)}$$

wherein $X_1$ and $X_2$ are the same or different and mean individually a halogen atom, $R_1$ denotes C$_5$ or C$_6$ cycloalkyl, halo-lower alkyl, lower alkenyl, lower-alkyl-substituted or unsubstituted phenyl, lower-alkoxyl substituted or unsubstituted benzyl group or a group —COR$_3$ in which R$_3$ is an alkyl group having at least five carbon atoms or a cyclo-C$_{3-6}$ alkyl, halo-lower alkyl, lower alkenyl, lower-alkyl- or lower-alkoxyl-substituted or unsubstituted phenyl, or lower-alkoxyl substituted or unsubstituted phenyl-lower alkyl, and R$_2$ stands for a hydrogen or halogen atom or a lower alkyl group.

* * * * *